United States Patent [19]

Schmidt et al.

[11] 4,127,728
[45] Nov. 28, 1978

[54] PREPARATION OF 1-PHENYL-2,2,2-TRIHALOGENO-ETHANOL ESTERS

[75] Inventors: Thomas Schmidt; Wolfgang Kramer; Eckart Kranz, all of Wuppertal, Germany

[73] Assignee: Bayer Aktiengesellschaft, Leverkusen, Germany

[21] Appl. No.: 717,302

[22] Filed: Aug. 24, 1976

[30] Foreign Application Priority Data

Sep. 12, 1975 [DE] Fed. Rep. of Germany ....... 2540653

[51] Int. Cl.$^2$ .................. C07C 67/14; C07C 67/08
[52] U.S. Cl. .................. 560/124; 560/11; 560/106; 560/228; 560/254; 260/340.5 R; 260/410.5; 260/456 P; 260/463; 260/465 D
[58] Field of Search ......... 260/488 CD, 468 H, 410.5, 260/456 P, 463, 465 D, 340.5; 560/11, 106, 228, 254

[56] References Cited

U.S. PATENT DOCUMENTS

3,801,712  4/1974  Meiser .................. 260/488 CD

OTHER PUBLICATIONS

Olah, "Friedel-Crafts and Related Reactions," vol. II, part I, pp. 616–621, 633–636 & 638–640 (1964).
Allinger, "Organic Chemistry," pp. 355–357 (1972).

*Primary Examiner*—James O. Thomas, Jr.
*Assistant Examiner*—Michael Shippen
*Attorney, Agent, or Firm*—Sprung, Felfe, Horn, Lynch & Kramer

[57] ABSTRACT

A process for the preparation of a substituted 1-phenyl-2,2,2-trihalo-ethanol ester of the formula

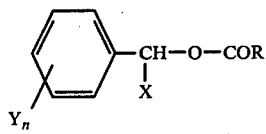

in which
R is alkyl, halogenoalkyl, alkoxy, cycloalkyl or optionally substituted phenyl, benzyl, phenoxy, or phenylsulfonyl,
X is halogenoalkyl with 1-3 carbon atoms and 1-3 halogen atoms,
Y is halogen, cyano, nitro, alkyl, alkoxy, alkylmercapto, sulfoalkoxy or optionally substituted methylenedioxy, and
n is an integer from 0 to 3, comprising reacting a compound of the formula

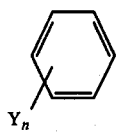

with a halogenated aldehyde of the formula

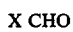

in the presence of a Friedel-Crafts catalyst at a temperature of about −70 to +100° C thereby to form a complex alcoholate, and reacting the complex alcoholate with an acid halide of the formula

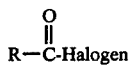

or with a corresponding acid anhydride at a temperature of about −70 to +100° C. The reaction with the acid halide or anhydride is preferably carried out in the presence of a solvent or diluent, sodium sulfate hydrate is added to the final reaction solution and the resulting mixture of sodium sulfate and basic aluminum halide is filtered off. The products are known insecticides.

10 Claims, No Drawings

PREPARATION OF 1-PHENYL-2,2,2-TRIHALOGENO-ETHANOL ESTERS

The present invention relates to an unobvious process for the preparation of certain known substituted 1-phenyl-2,2,2- trihalogeno-ethanol esters, which can be used as insecticides.

It has been disclosed in German Published Specification DOS 2,110,056 and by Pierre Crooy, C.A. 70, 67,818 m, J. W. Howard, J. Amer. Chem. Soc. 57,2317 (1935), T. C. Chen and W. T. Sumerford, J. Amer. Chem. Soc. 72, 5124 (1950), J. W. Howard and G. N. Stephens, J. Amer. Chem. Soc. 60, 228 (1938), and M. J. Kolbezen, F. A. Gunther, R. C. Blinn and G. E. Carman, J. Amer. Chem. Soc. 77, 5410 (1955) that substituted 1-phenyl-2,2,2-trihalogeno-ethanol esters can be prepared when the corresponding carbinols are esterified by means of an acid anhydride or acid chloride, if necessary in the presence of an acid-binding agent or in the presence of catalytic amounts of an acid, such as, for example, sulfuric acid.

The carbinols, which are to be used as starting materials, are prepared by a Friedel-Crafts reaction of the corresponding hydrocarbons with trihalogenoacetaldehydes under the catalytic co-action of aluminum chloride, iron-III chloride, boron trifluoride or concentrated sulfuric acid (compare the abovementioned literature sources; R. Riemschneider, Monatshefte fur Chemie 82, 600 (1951) and W. Reeve, J. P. Mutchler and CH.L. Liotta, Can.J.Chem. 44, 575 (1966)).

The two-stage process which is seen from the literature sources is illustrated by the following reaction equations, using 1-(3,4-dichlorophenyl)-2,2,2-trichloroethanol acetate as an example:

1st Stage

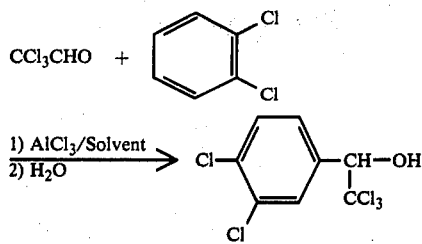

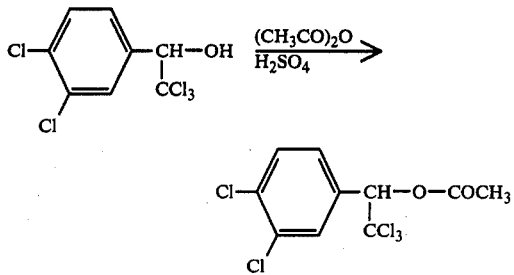

In the 1st stage, the reaction of trihalogenoacetaldehyde with optionally substituted benzenes in the presence of aluminum chloride represents the most advantageous process for the preparation of the carbinols.

However, this process has various disadvantages. Thus, mixtures of substances frequently arise and this leads to a lowering of the yields and to difficulties in isolating the carbinols in a pure form. In general, the yields are between 30 and 60% and only in isolated cases, such as in the case of phenyltrichloromethylcarbinol, are they around 80%.

In the 2nd stage the yields obtained are also in the majority of cases only between 35 and 70% and are over 80% only in exceptional cases. The overall yields from the two processes are therefore fairly low.

A further disadvantage of the 2nd stage lies in the high temperatures of about 120° to about 200° C which are required for carrying out this stage. Therefore, side reactions, which lead to undesirable, colored impurities, arise to an increasing extent in this stage and due to these the yield is further reduced and a further purification of the end products becomes necessary.

It has now been found that the known substituted 1-phenyl-2,2,2-trihalogeno-ethanol esters of the formula

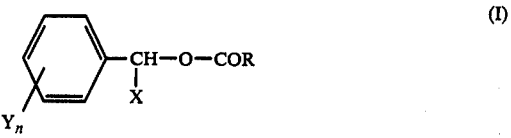

in which
R is alkyl, halogenoalkyl, alkoxy, cycloalklyl or optionally substituted phenyl, benzyl, phenoxy, or phenylsulfonyl,
X is halogenoalkyl with 1-3 carbon atoms and 1-3 halogen atoms,
Y is halogen, cyano, nitro, alkyl, alkoxy, alkylmercapto, sulfoalkoxy or optionally substituted methylenedioxy, and
n is an integer from 0 to 3,
are obtained when compounds of the formula

in which
Y and n have the above-mentioned meanings, are reacted with halogenated aldehydes of the formula

X—CHO  (III)

in which
X has the above-mentioned meaning,
in the presence of Friedel-Crafts catalysts at temperatures between about −70 and +100° C and the complex alcoholate thus formed is reacted with acid halides of the formula

in which
R has the abovementioned meaning and
Z represents halogen, especially chlorine or bromine, or with the corresponding acid anhydrides, optionally in the presence of a solvent or diluent, at temperatures between about −70 and +100° C.

It is extremely surprising that the reaction according to the invention can be carried out as a "one-pot reaction" without it being necessary to isolate the carbinol after the 1st reaction step. Thus, it could not be expected that the alcoholate complex of aluminum chloride and phenyltrihalogenoethanol, which is formed in the 1st reaction step, is so stable under the given reaction conditions that it neither forms the carbinol immediately nor that it forms tetrachloroethylbenzene in another secondary reaction. Since it was known that the reaction of the carbinol with an acid chloride or acid anhydride proceeds only at elevated temperature, it could not be expected that it is possible to carry out the process according to the invention at so low a temperature.

Since it was known that these esterification reactions frequently give colored by-products, it could not be expected that a reaction in which the starting materials are used without being isolated and without being purified gives end products in a good yield and in high purity.

The single stage process according to the invention has a number of advantages. Compared with the known two-stage process it is simpler, less time-consuming and more economical.

The process according to the invention can be carried out at lower temperatures than the known process.

The resulting products are, moreover, only slightly colored and the purity, which in some cases is more than 99%, is far higher than was possible according to the known process.

The complex formed during the Friedel-Crafts reaction reacts completely with acid halides or acid anhydrides, which is evident from the fact that no further carbinol can be detected in the product mixture after the acetylation and hydrolysis.

If o-dichlorobenzene and chloral, in the presence of aluminum chloride as the catalyst, and acetic anhydride are used as the starting materials, the course of the reaction can be represented by the following equation:

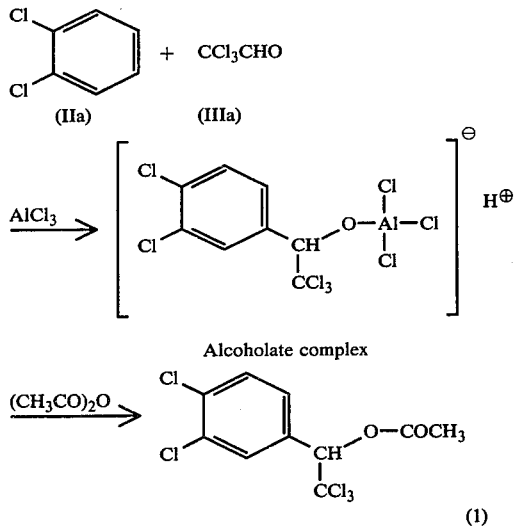

Formula (II) gives a general definition of the hydrocarbons to be used as starting materials. In formula (II), Y preferably represents chlorine or bromine and especially represents chlorine, and also represents alkyl, alkoxy and alkylthio with, in each case, 1 to 4 carbon atoms, and especially represents methyl or methoxy. In addition, Y preferably represents methylenedioxy, which can optionally be sbustituted by methyl or ethyl, and also represents nitro or cyano or sulfo-lower alkoxy. The compounds are generally known products in organic chemistry.

Examples which may be mentioned are: benzene, bromobenzene, nitrobenzene, benzonitrile, iodobenzene, phenyl ethyl ether, o-bromo-chloro-benzene, o-chloro-nitrobenzene, o-ethoxynitrobenzene, o-nitrobenzenesulfonic acid methyl ester, o-nitro-bromobenzene, o-chloro-benzonitrile, o-chlorotoluene, o-nitrotoluene, m-chloro-bromobenzene, m-ethoxychlorobenzene, m-chloro-nitrobenzene, m-ethoxy-nitrobenzene, m-nitro-toluene, m-ethoxybenzonitrile, methylenedioxybenzene, pyrocatechol diethyl ether and pyrocatechol dimethyl ether.

The halogenated aldehydes to be used as starting materials are defined by the formula (III). In this formula, X preferably represents trichloromethyl, tribromomethyl or trifluoromethyl. The compounds are generally known products.

Examples which may be mentioned are: trichloroacetaldehyde, tribromoacetaldehyde, trifluoroacetaldehyde, bromodichloro-acetaldehyde, dibromo-chloro-acetaldehyde, chloro-difluoro-acetaldehyde, bromo-difluoro-acetaldehyde, dichloro-fluoro-acetaldehyde, dibromo-fluoro-acetaldehyde, bromo-chloro-fluoro-acetaldehyde, 2,2-dichloropropionaldehyde, 2,2-dibromoacetaldehyde, 2-chloroisobutyraldehyde and 2-bromoisobutyraldehyde.

The formula (IV) gives a general definition of the acid halides (and the corresponding acid anhydrides) which are also required as starting materials. In this formula, R preferably represents straight-chain or branched alkyl with up to 15 carbon atoms; halogenoalkyl with, preferably, 1 to 4, and especially 1 or 2, carbon atoms and preferably 1 to 5, and especially 1 to 3, halogen atoms, the halogen atoms preferably being fluorine, chlorine and bromine. R also preferably represents alkoxy with 1 to 4 carbon atoms; cycloalkyl with 3 to 6 carbon atoms or optionally substituted phenyl, benzyl, phenoxy or phenylsulfonyl, possible substituents being, preferably: halogen, especially fluorine, chlorine or bromine, and also alkyl with 1 to 2 carbon atoms. These compounds are generally known and readily accessible substances. Examples which may be mentioned are: acetyl chloride, propionyl chloride, butyryl chloride, iso-butyryl chloride, n-butanecarboxylic acid chloride, sec.-butanecarboxylic acid chloride, tert.-butanecarboxylic acid chloride, cyclopropanecarboxylic acid chloride, chloroacetic acid chloride, chloropropionic acid chloride, dichloroacetic acid chloride, trichloroacetic acid chloride, benzyl chloride, acetyl bromide, propionyl bromide, chloroacetic acid bromide, acetyl fluoride, propionyl fluoride and corresponding anhydrides.

Catalysts which can be used for the process according to the invention are the known Lewis acids. These include, preferably, metal halides, such as, for example, aluminum chloride, aluminum bromide, antimony pentachloride, iron-III chloride, iron-III bromide, boron trifluoride, boron trichloride, boron tribromide and tin tetrachloride.

Diluents which can be used for the process according to the invention are organic solvents which are inert towards the particular Lewis acids used as catalysts. These solvents include, preferably, aliphatic and aromatic hydrocarbons, such as, for example, pentane, petroleum ether, cyclohexane and benzene; chlorinated hydrocarbons, such as, for example, chloroform, carbon tetrachloride, dichloroethane, chlorobenzene and dichlorobenzene; nitrated hydrocarbons, such as, for example, nitromethane, nitroethane, nitropropane and nitrobenzene; ethers, such as, for example, diethyl ether; and also carbon disulfide, dimethylsuloxide, sulfur dioxide and tetramethylenesulfone. The hydrocarbons (II), which are to be used as starting materials, can, however, also serve as the solvent or diluent when used in excess.

The process according to the invention is carried out at temperatures between $-70$ and $+100°$ C, preferably between about $-10$ and $+25°$ C.

When carrying out the process according to the invention, about 1 mole of the halogenated aldehyde of the formula (III), about 1 mole of the catalyst and about 0.8 to 1.2 moles of the acid halide or acid anhydride are employed per 1 to 2 moles of the hydrocarbon of the formula (II).

In order to isolate the compounds of the formula (I), the entire reaction solution can be poured onto ice and the end product isolated from the organic phase by customary methods. When an aluminum halide is used as the catalyst, an effluent is obtained which, above all because of its content of aluminum salts, cannot be discharged without working up. A method of working up has been found which does not produce effluent. This is achieved when a freshly prepared saturated aqueous solution of sodium sulfate is added dropwise to the reaction mixture. The solid precipitate of a basic aluminum halide and $Na_2SO_4\cdot(H_2O)_x$, which is thus obtained, can be filtered off. The entire amount of water previously used to dissolve sodium sulfate is contained in this precipitate, bound as water of crystallization. The desired compound of the formula (I) is isolated from the organic phase by customary methods.

The advantage of this method of working up is that it manages without effluent and that the aluminum salts which necessarily result are obtained in a solid form.

Alternatively, a procedure, in which, after the acid halide (acid anhydride) has been added dropwise, the entire reaction mixture is added to a suspension of Glauber's salt ($Na_2SO_4\cdot10\ H_2O$) in an inert solvent, can be used. In this case also a solid precipitate of a basic aluminum halide and sodium sulfate $\cdot(H_2O)_x$ is obtained and can be filtered off. The compound of the formula (I) is isolated from the organic phase by customary methods (see the description in the examples).

The substituted 1-phenyl-2,2,2-trihalogeno-ethanol esters of the formula (I), which are obtainable by the process according to the invention, display a strong insecticidal action, especially against flies, gnats and bugs (compare German Patent Specifications 673,246 and 706,111, German Published Specification DOS 2,110,056, T. C. Chen and W. T. Sumerford, J. Amer. Chem. Soc. 72, 5124 (1950) and M. J. Kolbezen, F. A. Gunther, R. C. Blinn and G. E. Carman, J. Amer. Chem. Soc. 77, 5410 (1955)).

The compounds produced according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, encrusting, dressing, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of compounds according to the present invention is illustrated, without limitation, in the following example:

EXAMPLE

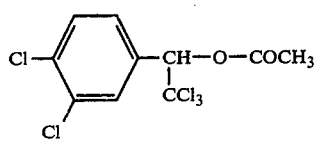

(1)

134 g (1 mole) of aluminum chloride are added, while stirring, to 500 ml (4.4 moles) of o-dichlorobenzene, the excess of which simultaneously serves as the solvent. The mixture is cooled to 0° C and 147.5 g (1 mole) of anhydrous chloral are added dropwise at 0° to 5° C. The mixture is allowed to react further at 0° to 5° C for 6 hours and 78 g (1 mole) of acetyl chloride (or 102 g, 1 mole of acetic anhydride) are then added dropwise at 0° to 8° C. The batch is then poured in portions into a suspension of 322 g (1 mole) of sodium sulfate ·10 $H_2O$ in o-dichlorobenzene and the temperature is kept at about 20° C by cooling. The salts which have precipitated out are filtered off and washed twice with 300 ml of o-dichlorobenzene and the solvent is stripped off at 100° C in a rotary evaporator. 100 ml of isopropanol are added to the residue and the mixture is left to crystallize out at 0° C. The crystals are filtered off, washed with a little cold isopropanol and dried in a vacuum desiccator. 309 g (92% of theory) of 1-(3,4-dichlorophenyl)-2,2,2-trichloro-ethyl acetate with a melting point of 85°–86° C are obtained.

The following compounds in the Table can be prepared in an analogous manner:

Table $$\underset{Y_n}{\diagup\!\!\!\diagup}\text{—CH—O—COR} \atop \phantom{xxxxxxxx}|\text{CX}_3$$

| Compound No. | Y | X | R | Boiling point (° C) | Melting point (° C) |
|---|---|---|---|---|---|
| 2 | 2,4-Cl$_2$ | Cl | C$_2$H$_5$ | 144–48/0.5 mm | |
| 3 | 3,4-Cl$_2$ | Cl | n-C$_3$H$_7$ | 145/0.4 mm | |
| 4 | 3,4-Cl$_2$ | F | CH$_3$ | 120/0.3 mm | |
| 5 | 3,4-Cl$_2$ | Br | CH$_3$ | 160/0.3 mm | |
| 6 | 3,4-Cl$_2$ | Cl | CH(CH$_3$)$_2$ | 145/0.5 mm | |
| 7 | 3,4-Cl$_2$ | Cl | C(CH$_3$)$_3$ | 150/0.4 mm | |
| 8 | 3,4-Cl$_2$ | Cl | CH(C$_2$H$_5$)$_2$ | 142/0.2 mm | |
| 9 | 2,4-Cl$_2$ | Cl | CH$_3$ | | 83–84 |
| 10 | 2,5-Cl$_2$ | Cl | CH$_3$ | | 92 |
| 11 | 2,4-Cl$_2$ | Cl | CH$_2$Br | | 98 |
| 12 | 3-Cl | Cl | CH$_3$ | | 59–60 |
| 13 | 3-Cl | Cl | n-C$_3$H$_7$ | 172–73/12 mm | |
| 14 | 3-Cl | Cl | n-C$_4$H$_9$ | 183–84/10 mm | |
| 15 | 3-Cl | Cl | ⬡ | | 92–93 |
| 16 | 3-Cl | Br | CH$_3$ | | 100–101 |
| 17 | 3-Cl | Br | n-C$_3$H$_7$ | | 61–62 |
| 18 | 3-Cl | Br | n-C$_4$H$_9$ | 193/25 mm | |
| 19 | 3-Cl | Br | ⬡ | | 114–115 |
| 20 | 4-CH$_3$ | Cl | CH$_3$ | | 105–106 |
| 21 | 4-CH$_3$ | Cl | n-C$_3$H$_7$ | | 59–60 |
| 22 | 4-CH$_3$ | Cl | n-C$_4$H$_9$ | 172–73/11 mm | |
| 23 | 4-CH$_3$ | Cl | ⬡ | | 94–95 |
| 24 | 4-CH$_3$ | Br | CH$_3$ | | 149–150 |
| 25 | 4-CH$_3$ | Br | n-C$_3$H$_7$ | | 170 |
| 26 | 4-CH$_3$ | Br | n-C$_4$H$_9$ | | 63 |
| 27 | 4-CH$_3$ | Br | ⬡ | | 126 |
| 28 | 4-Cl | Cl | CH$_3$ | | 123–124.5 |
| 29 | 4-Cl | Cl | CH$_2$Cl | | 90.5–91.5 |
| 30 | 4-Cl | Cl | —CH$_2$—⬡ | | 62–64 |
| 31 | 4-Cl | Cl | (Cl-substituted benzyl) | | 103–104.5 |
| 32 | 4-Cl | Cl | —⬡—Cl | | 145–155 |
| 33 | 4-Cl | Cl | ⬡ | | 128–129 |
| 34 | 4-Cl | Cl | C$_2$H$_5$ | | 77.5–78.5 |
| 35 | 4-Cl | Cl | n-C$_3$H$_7$ | 148/2 mm | |
| 36 | 4-Cl | Cl | i-C$_3$H$_7$ | | 66.5–68 |
| 37 | 4-Cl | Cl | n-C$_4$H$_9$ | | 47.5–48.5 |
| 38 | 4-Cl | Cl | i-C$_4$H$_9$ | | 41.5–42.5 |
| 39 | 4-Cl | Cl | C(CH$_3$)$_3$ | | 92.5–93.5 |
| 40 | 4-Cl | Cl | n-C$_5$H$_{11}$ | | 36–37 |

Table-continued

| Compound No. | Y | X | R | Boiling point (°C) | Melting point (°C) |
|---|---|---|---|---|---|
| 41 | 4-Cl | Cl | ⟨H⟩ | | 60–61 |
| 42 | 4-Cl | Cl | n-C$_7$H$_{15}$ | | 43–44 |
| 43 | 4-Cl | Cl | n-C$_{11}$H$_{23}$ | | 40–41 |
| 44 | 4-Cl | Cl | n-C$_{15}$H$_{31}$ | | 53–53.5 |
| 45 | | Cl | CH$_3$ | | 89 |
| 46 | 2,4-Cl$_2$ | Cl | C$_2$H$_5$ | 140–148/0.7 mm | |
| 47 | 3,4-Cl$_2$ | Cl | OCH$_3$ | 140/0.5 mm | |
| 48 | 3,4-Cl$_2$ | Cl | ⟨⟩ | 190–195/0.5 mm | |
| 49 | 4-OCH$_3$ | Cl | CH$_3$ | | 83 |
| 50 | 3,4-Cl$_2$ | Cl | OC$_4$H$_9$ | 163–165/0.6 mm | |
| 51 | 3,4-Cl$_2$ | Cl | ▷ | | 63 |
| 52 | 3,4-Cl$_2$ | Cl | C$_2$H$_5$ | 145/0.5 mm | |

It will be appreciated that the instant specification and examples are set forth by way of illustration and not limitation, and that various modifications and changes may be made without departing from the spirit and scope of the present invention.

What is claimed is:

1. A process for the preparation of a 1-phenyl-2,2,2-trihalo-ethanol ester of the formula

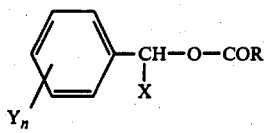

in which
R is alkyl, halogenoalkyl, alkoxy, cycloalkyl, or optionally substituted phenyl, benzyl, phenoxy or phenylsulfonyl wherein the substituent is halogen or alkyl with 1 to 2 carbon atoms,
X is trichloromethyl, tribromomethyl, bromodichloromethyl, dibromo-chloromethyl, chlorodifluoromethyl, bromo-difluoromethyl, dichlorofluoromethyl, dibromo-fluoromethyl, bromochloro-fluoromethyl, 1,1-dichloroethyl, dibromomethyl, 1-chloroisopropyl or 1-bromoisopropyl,
Y is chlorine, bromine, cyano, nitro, alkyl, alkoxy, alkylmercapto, sulfoalkoxy or optionally substituted methylenedioxy, and
n is an integer from 0 to 3,
comprising reacting about 1 to 2 molar amounts of a compound of the formula

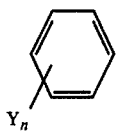

with about 1 molar amount of a halogenated aldehyde of the formula

X CHO in the presence of about 1 molar amount of a metal halide Friedel-Crafts catalyst at a temperature of about −70 to +100° C thereby to form a complex alcoholate of said catalyst, and reacting the complex alcoholate with about 0.8 to 1.2 molar amounts of an acid halide of the formula $$R-\overset{O}{\underset{\|}{C}}-Halogen$$

or with a corresponding acid anhydride at a temperature of about −70 to +100° C.

2. The process according to claim 1, in which the reactions are carried out at a temperature of about −10° to +25° C.

3. The process according to claim 1, in which sodium sulfate is added to the final reaction solution and the resulting mixture of sodium sulfate and basic aluminum halide is filtered off.

4. The process according to claim 1, in which the reaction with the acid halide or anhydride is carried out in the presence of a solvent or diluent.

5. The process according to claim 2, in which
R is alkyl with up to 15 carbon atoms; halogenoalkyl with up to 4 carbon atoms and up to 5 halogen atoms; alkoxy with up to 4 carbon atoms; cycloalkyl with 3 to 6 carbon atoms; or phenyl, benzyl, phenoxy or phenylsulfonyl each optionally substituted with at least one of halogen and alkyl with up to 2 carbon atoms;
X is methyl substituted with three halogen atoms selected from the group consisting of chlorine, bromine and fluorine;
Y is chlorine; bromine; alkyl, alkoxy or alkylmercapto each with up to 4 carbon atoms; methylenedioxy optionally substituted with methyl or ethyl; nitro; or cyano; and
n is 0, 1 or 2,
the second reactant is the acid chloride, bromide or anhydride, sodium sulfate is added to the final reaction solution and the resulting mixture of sodium sulfate and basic aluminum halide is filtered off.

6. The process according to claim 1, in which the end product is 1-(3,4-dichlorophenyl)-2,2,2-trichloro-ethyl acetate of the formula

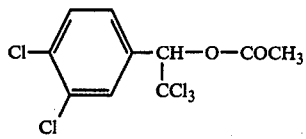

7. The process according to claim 1, in which the end product is 1-(3,4-dichlorophenyl)-2,2,2-trichloro-ethyl isobutyrate of the formula

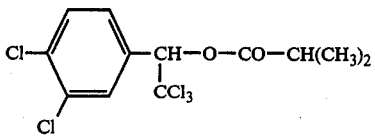

8. The process according to claim 1, in which the end product is 1-(2,4-dichlorophenyl)-2,2,2-trichloro-ethyl acetate of the formula

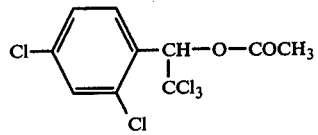

9. The process according to claim 1, in which the end product is 1-(3,4-dichlorophenyl)-2,2,2-trichloro-ethyl cyclopropylcarboxylate of the formula

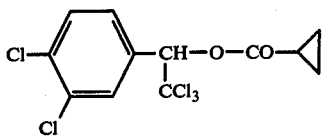

10. The process according to claim 1, in which the end product is 1-(3,4-dichlorophenyl)-2,2,2-trichloro-ethyl propionate of the formula

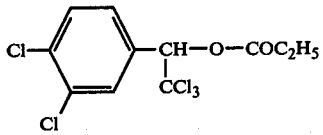

* * * * *